United States Patent [19]
Dubourdieu et al.

[11] Patent Number: 6,139,891
[45] Date of Patent: Oct. 31, 2000

[54] BIOLOGICAL SUBSTANCE FOR THE PHYSICO-CHEMICAL STABILIZATION OF WINES

[75] Inventors: Denis Dubourdieu, Beguey; Virginie Moine, Pessac, both of France

[73] Assignee: Faculte d'Oenologie, Talence, France

[21] Appl. No.: 08/817,937

[22] PCT Filed: Oct. 27, 1995

[86] PCT No.: PCT/FR95/01426

§ 371 Date: Apr. 30, 1997

§ 102(e) Date: Apr. 30, 1997

[87] PCT Pub. No.: WO96/13571

PCT Pub. Date: May 9, 1996

[30] Foreign Application Priority Data

Oct. 31, 1994 [FR] France ................................ 94 13261

[51] Int. Cl.[7] .............................. C12G 1/10; C12G 1/12; C12H 1/10
[52] U.S. Cl. ......................... 426/330.4; 426/60; 426/424
[58] Field of Search .................................. 426/330.4, 60, 426/424

[56] References Cited

PUBLICATIONS

Cameron et al, The Mannoprotein of Sacch. cer. is an Effective Bioemulsifier, Applied Environmental Micro., Jun. 1988, pp. 1420–1425.

Bouton et al, Principles and Practices of Winemaking, Chapman & Hall Enology Library, 1986, pp. 90–91.

Wucherpfennig et al, Effect of Colloidal Substances Originating from Yeast on Wine Filterability, Zeitschrift fuer Lebensmittel–Untersuchung und–Forschung 1984, 179 (2) pp. 119–124.

Vine, R., Commercial Winemaking, AVI Publishing Co., Wesport Conn., 1981, pp. 161–164.

Villettaz et al, Am. J. Enol. Vitic., vol. 35, No. 4, 1984, pp. 253–256.

*Primary Examiner*—Curtis E. Sherrer
*Attorney, Agent, or Firm*—Young & Thompson

[57] ABSTRACT

A treatment for stabilizing wine against tartaric acids and proteins by adding mannoproteins extracted from yeast walls by enzymatic digestion, is disclosed. A method for carrying out the treatment by extracting mannoproteins from yeast by enzymatic digestion, and the resulting mannoprotein, are also disclosed.

5 Claims, 6 Drawing Sheets

* spectrophotometric at 225 nm (proteins)
• refractometric detection (polysaccharides)

* spectrophotometric detection at 225 nm (proteins)
• refractometric detection (polysaccharides)

BIOLOGICAL SUBSTANCE FOR THE PHYSICO-CHEMICAL STABILIZATION OF WINES

CROSS REFERENCE TO RELATED APPLICATION

This application is the 35 USC 371 national stage of international application PCT/FR95/01426 filed on Oct. 27, 1995, which designated the United States of America.

FIELD OF THE INVENTION

The present invention relates to a biological substance for the treatment of wine and, more particularly, to improve the protein stability of white and rose wines and to prevent tartaric precipitations in white, rose and red wines.

BACKGROUND OF THE INVENTION

It is known that the marketing of bottled wines requires not only that the wine be clear at the time of bottling but that it remain so for a period of time, especially so in the case of wines which are stored for relatively long periods of time.

Now, it is known that current wine stabilization treatments are not very satisfactory, whether this is in regard to precipitations of tartaric salts or those of proteins, referred to in the field of oenology as "tartaric and proteinic spoilage".

In fact, during the storage of white wines, proteinic spoilage results in cloudiness or specific deposits which appear in the bottle when the storage temperature of the wine is elevated and/or as a result of the wine being enriched with the tannins from the cork.

A known solution involves treating the musts and the wines with bentonite, but the dosages necessary in terms of the requirements may be sufficiently high to detract from the organoleptic characteristics of the wines thus treated.

Other attempts were made along enzymatic lines, using exogenic proteases, or on the basis of yeast, in order to eliminate the proteins responsible for the proteinic spoilage, but the results were not satisfactory.

It was recently shown by the inventors of the present application that, in the course of the storage of white wines on the lees, the noted improvement of the proteinic stability of white wines was due to the presence of mannoproteins released by the yeasts.

With regard to the precipitation of tartaric salts, which are present essentially in the form of potassium acid tartrate, they are in a state of supersaturation in the wines. In addition, during storage of the wine in winter, the cold causes crystalline precipitations, but in any event this precipitation also occurs in the course of time and is visible in the bottles.

Ways in which to stabilize these tartaric salts have been sought and at present three are known.

The first solution involves accelerating the precipitation by maintaining the wine for a number of weeks at negative temperatures, then filtering the wine to withdraw the crystals.

The second solution involves improving on the first solution, by adding elevated doses of crystals to the wine such that the low temperature treatment is rendered more effective and its duration is shorter, but filtration remaining obligatory in order to withdraw the additional crystals and the crystals which have developed.

The third solution involves the addition of mesotartaric acid to the wine, which acid counteracts the crystallization of the tartaric acids under the low temperature effects. The protective effect disappears as soon as the mesotartaric acid hydrolizes, which takes place all the more rapidly the higher the storage temperature of the wine.

These solutions are not satisfactory, because the first two are lengthy and costly in addition to altering the organoleptic characteristics of the wine treated.

With regard to the third solution, its effectiveness is of short duration, and is therefore restricted to wines intended for early consumption, in addition to the fact that it is necessary to introduce into the wine a foreign compound which is initially not contained therein.

More recent tests have shown that the mannoproteins extracted under heat from the cell walls of the yeast belonging to the species *Saccharomyces cerevisiae* have an inhibitive effect on the crystallization of tartaric salts.

The process to obtain these mannoproteins involves rendering them soluble with heat at 100° C. in an aqueous medium and to collect them, either directly by lyophilization, or by precipitation with ethanol and by drying the precipitate after centrifugation.

Yet, the effectiveness of the proposed preparations when tested in a model medium was not verified in respect of the majority of wines. Moreover, said preparation of mannoproteins does not contribute any improvement to the proteinic instability of white wines.

SUMMARY OF THE INVENTION

The object of the present invention is to provide a treatment for wines, whether white, red or rose, in order to stabilize them with respect to tartaric and proteinic precipitations, with a sufficiently long-term effect to be regarded as permanent. In addition, the treatment provides for the addition of a biological substance obtained by a process according to the invention, i.e. introducing a substance which is permitted by the laws controlling wines, said biological substance being odourless and completely soluble in the wines.

According to the present invention, the treatment of a wine for stabilizing it in respect of tartaric and proteinic salts includes the addition, to the wine, of mannoproteins extracted from the cell walls of yeast by enzymatic digestion.

This treatment, more particularly, involves the addition, to the wine, of mannoproteins extracted from the cell walls of yeast by enzymatic digestion using a mixture of β-1-3 and β-1-6 glucanases.

According to the invention, the yeasts used belong to the species *Saccharomyces cerevisiae* and the quantity of mannoproteins used in the wine is less than 30 g/hl.

The invention also relates to a process for the extraction of mannoproteins by enzymatic digestion of yeast for use in the treatment according to the invention, wherein:

the yeast cell walls are incubated in an aqueous medium in the presence of β-glucanase,
solid matter is separated,
the liquid phase is concentrated, in particular by ultrafiltration,
an additional step involves drying the product obtained, in particular by lyophilization or atomization, for example to ensure comfortable handling.

The process according to the invention is characterized in that the β-glucanases used are of the β-1-3 and β-1-6 glucanase type.

The invention also provides a mannoprotein obtained by said extraction process for use in the treatment process according to the invention, wherein the analysis of the mannoprotein by high-pressure liquid chromatography for molecular separation shows the presence of a characteristic peak, wherein the analysis by sodium dodecyl sulfate polyacrylamide gel electrophoresis shows the presence of two proteins of 41 600 and 31 800 dalton, and wherein the analysis by capillary electrophoresis shows the presence of a characteristic peak of 31 800 dalton corresponding to mannoprotein.

BRIEF DESCRIPTION OF THE DRAWINGS

The treatment according to the present invention is described hereinafter together with a specific embodiment of the process for the extraction of the mannoproteins necessary to this treatment.

DETAILED DESCRIPTION OF THE INVENTION

The process according to the invention is now described below with reference to a specific embodiment.

Cell walls of yeast, more particularly *Saccharomyces cerevisiae*, are incubated at 40° C. in water, in the presence of a preparation of β-glucanase, in particular that marketed by the company Novo under the name Glucanex.

This preparation comprises exo-β-(1-3)-glucanase, endo-β-(1-3)-glucanase and exo-β-(1-6)-glucanase activities.

Subsequently, the solid matter is separated.

The liquid phase is then concentrated, in particular by ultrafiltration.

The dry mass of the product corresponds substantially to 50% of the mass of the cell walls initially introduced into the preparation.

The product is composed of 88% polysaccharides and 4% proteins, with 8% being undetermined, without doubt being due to the hydration of the product.

The product is odourless, soluble in water and wines and does not clog up the filtering surfaces used for the filtration of the wines.

Figure 1:
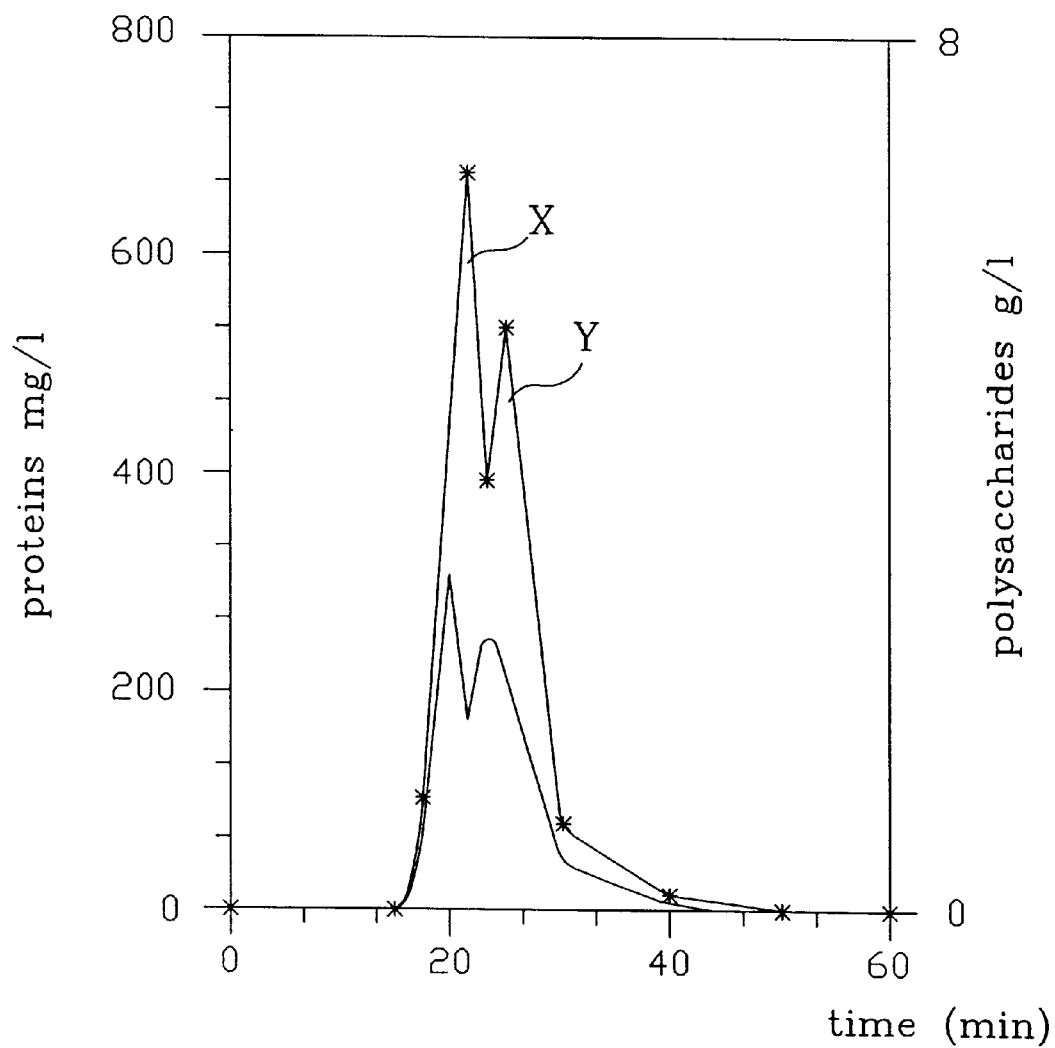
FIG. 1 shows a chromatogram from high-pressure liquid chromatography in the separation of mannoproteins extracted by enzymatic digestion.
Figure 2:
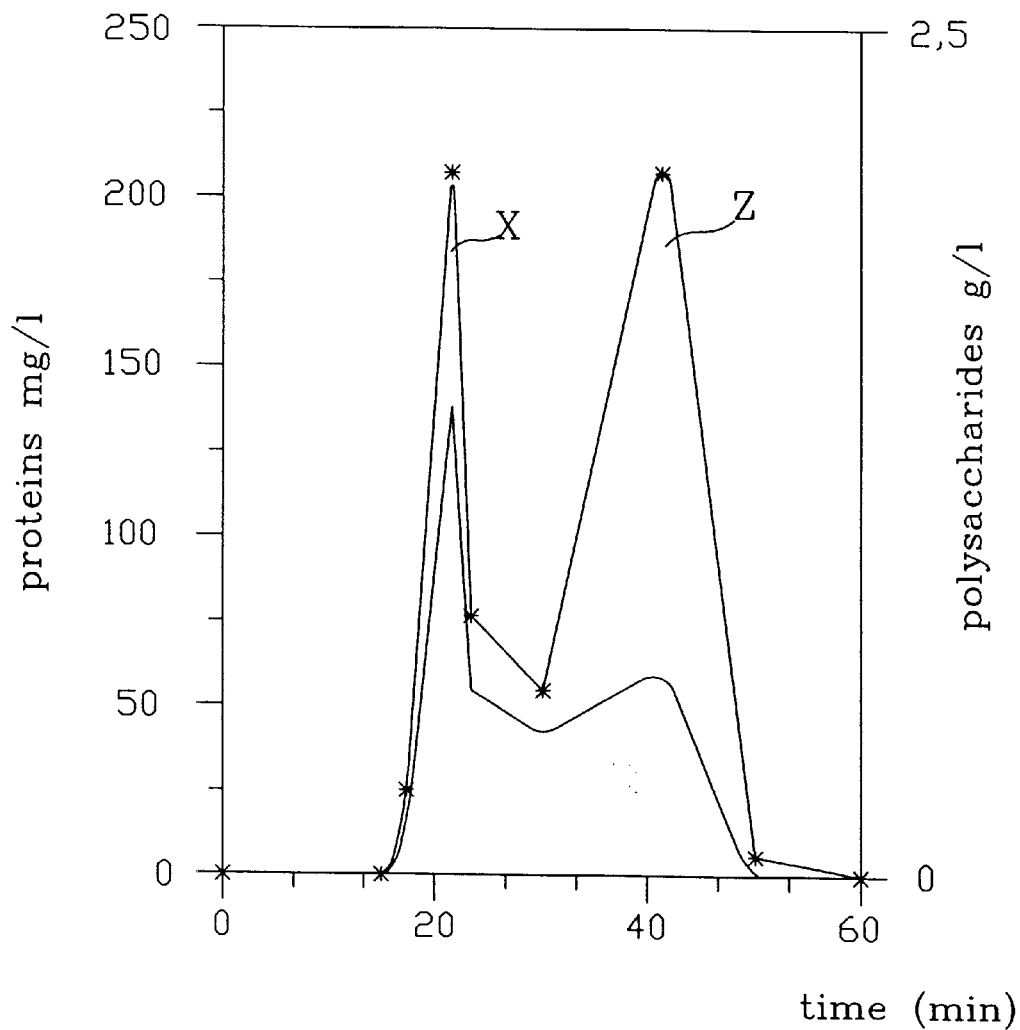
FIG. 2 shows a chromatogram of mannoproteins extracted by heat.
Figure 3:
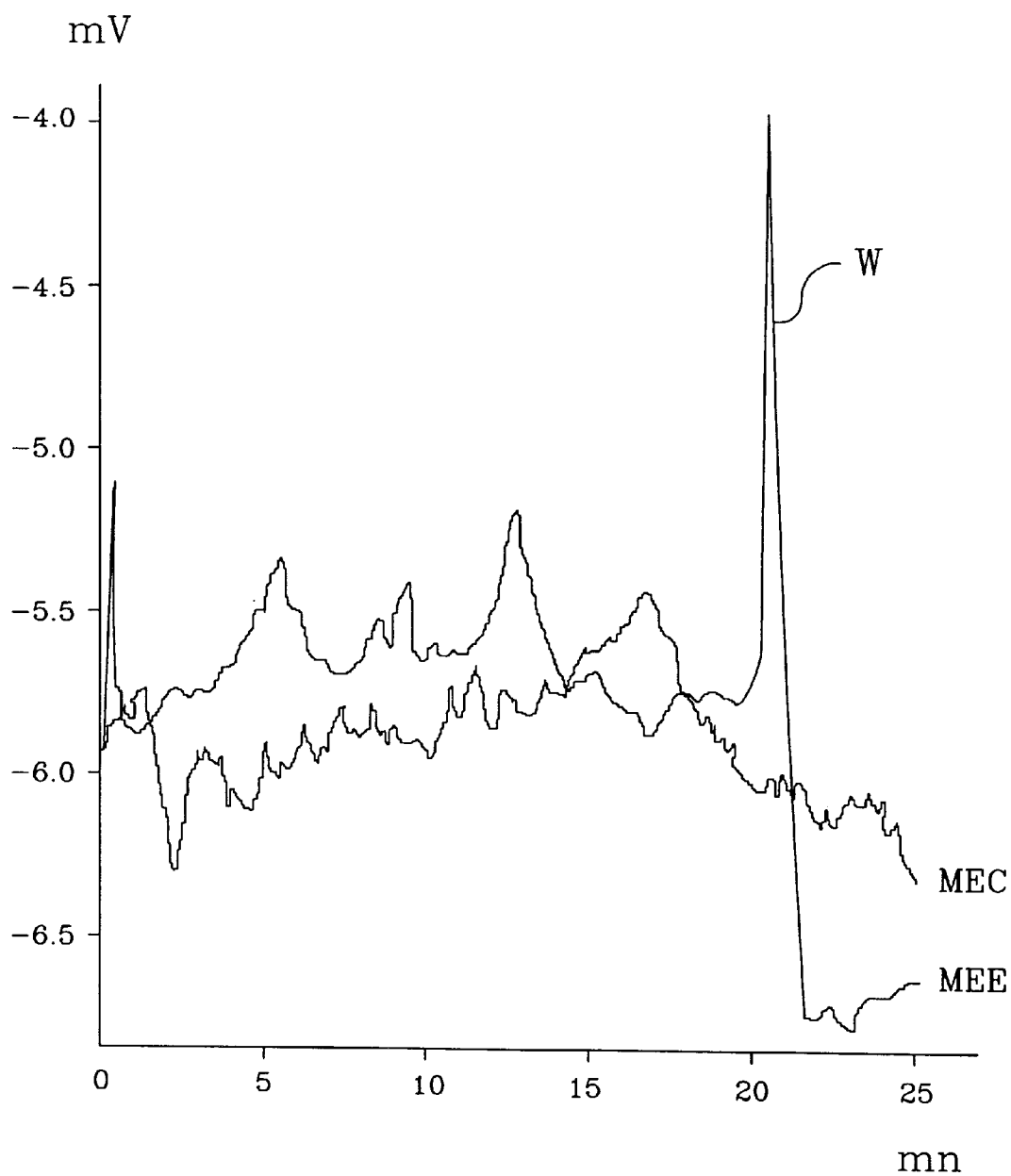
FIG. 3 shows a graph obtained by capillary electrophoresis of the mannoproteins extracted by enzymatic digestion (MEE) compared to the graph of mannoproteins extracted by heat (MEC)

Referring to FIGS. 1 and 2, a considerable difference will be noted between the graphs which are plotted for each of these Figures by the spectrophotometric detection at 225 nm for the proteins, and by refractometric detection for the polysaccharides.

Indeed, the graph of FIG. 2 shows a first peak (X) which corresponds to the empty volume of the column, and a second peak (Z) which corresponds to the total volume of the column.

It will be noted that the graph of FIG. 1 shows a second peak (Y) in the immediate proximity of the peak (X) of the empty volume of the column, which is absent in the graph of FIG. 2.

The process according to the invention permits the extraction and the conserving of a specific mannoprotein.

On the other hand, analyzed by capillary electrophoresis, under non-distorted conditions, over a column of molten silica, the mannoproteins, which are extracted by enzymatic digestion, show a peak (W) which corresponds to the mannoprotein which is responsible for the thermostabilization of the proteins of white wine. On the other hand, this peak is absent during the analysis of the mannoproteins extracted by heat, also using capillary electrophoresis.

Subsequently, tests were carried out to verify the effects of the mannoproteins extracted by enzymatic means, based on different strains of yeast all belonging to the species *Saccharomyces cerevisiae*, referred to as "MEE", with regard to the tartaric stabilization, on the one hand, and with regard to the proteinic stabilization, on the other hand.

I/ Tartaric Stabilization

Two types of test are known:

1.—Determining the tartaric stability index

Cream of tartar is introduced to the samples to be tested, in variable quantities, solubilized by heating at 30° C. and then cooled to −4° C.

The more stable the medium, the greater the quantity of cream of tartar required to bring about the crystallization.

Estimation of the crystallization is carried out visually or by determining by flame photometry the difference in concentration of the potassium in the filtered wine before and after passing to the cold.

A wine is considered to be stable if the addition of 75 mg of cream of tartar for 100 ml of the sample does not cause crystallization.

Test in a model medium

The test results are given below, basing them on 100 ml of a model hydroalcoholic medium composed of:

1.1 g/l of potassium chloride, 2.1 g/l of tartaric acid, and 10.5% of ethanol.

The variable parameter is the quantity of potassium hydrogentartrate, added in dosages of: 0, 50, 75, 100 and 125 mg.

The samples are tested comparatively with the addition of mesotartaric acid, mannoproteins extracted by heat (MEC) and three sorts of mannoproteins extracted by enzymatic digestion (MEE).

The results in the following Table show the differences in the potassium concentration (mg/l) of the samples before and after cooling down.

| THK mg/100 ml | 0 | 50 | 75 | 100 | 125 |
|---|---|---|---|---|---|
| Reference | 0 | 0 | 40 | 100 | 180 |
| Meso. acid 5 g/hl | 0 | 0 | 0 | 0 | 0 |
| Meso. acid 10 g/hl | 0 | 0 | 0 | 0 | 0 |
| Meso. acid 25 g/hl | 0 | 0 | 0 | 0 | 0 |

-continued

|  | | | | | |
|---|---|---|---|---|---|
| MEC 10 g/hl | 0 | 0 | 30 | 100 | 180 |
| MEC 25 g/hl | 0 | 0 | 0 | 20 | 100 |
| MEC 50 g/hl | 0 | 0 | 0 | 0 | 40 |
| MEE1 10 g/hl | 0 | 0 | 0 | 60 | 120 |
| MEE1 25 g/hl | 0 | 0 | 0 | 60 | 100 |
| MEE1 50 g/hl | 0 | 0 | 0 | 40 | 100 |
| MEE2 10 g/hl | 0 | 0 | 60 | 80 | 120 |
| MEE2 25 g/hl | 0 | 0 | 0 | 0 | 60 |
| MEE2 50 g/hl | 0 | 0 | 0 | 0 | 0 |
| MEE3 10 g/hl | 0 | 0 | 80 | 120 | 180 |
| MEE3 25 g/hl | 0 | 0 | 0 | 60 | 180 |
| MEE3 50 g/hl | 0 | 0 | 0 | 0 | 180 |

It will be seen that the precipitation of cream of tartar in the synthetic medium is completely inhibited by the mesotartaric acid, but also by the mannoproteins extracted by enzymatic action, although the effectiveness, at identical doses, is slightly lower.

Test with a white wine

The following Table shows the results obtained with mesotartaric acid, the mannoproteins extracted with heat and the mannoproteins extracted by enzymatic digestion.

|  | | | | | |
|---|---|---|---|---|---|
| THK mg/100 ml | 0 | 50 | 75 | 100 | 125 |
| Reference | 0 | 20 | 40 | 60 | 80 |
| Meso. acid 5 g/hl | 0 | 0 | 0 | 20 | 20 |
| Meso. acid 10 g/hl | 0 | 0 | 0 | 0 | 0 |
| Meso. acid 25 g/hl | 0 | 0 | 0 | 0 | 0 |
| MEC 10 g/hl | 0 | 20 | 40 | 40 | 60 |
| MEC 25 g/hl | 0 | 20 | 20 | 20 | 60 |
| MEC 50 g/hl | 0 | 0 | 40 | 40 | 40 |
| MEE1 10 g/hl | 0 | 20 | 20 | 20 | 20 |
| MEE1 25 g/hl | 0 | 0 | 0 | 60 | 100 |
| MEE1 50 g/hl | 0 | 0 | 0 | 0 | 0 |
| MEE2 10 g/hl | 0 | 0 | 0 | 20 | 60 |
| MEE2 25 g/hl | 0 | 0 | 0 | 0 | 20 |
| MEE2 50 g/hl | 0 | 0 | 0 | 0 | 20 |
| MEE3 10 g/hl | 0 | 0 | 0 | 20 | 20 |
| MEE3 25 g/hl | 0 | 0 | 0 | 0 | 40 |
| MEE3 50 g/hl | 0 | 0 | 0 | 0 | 40 |

It will be seen that the reference sample shows a tartaric precipitation from the addition of 50 mg/l which is the sign of a particularly unstable wine.

The mesotartaric acid and one of the mannoproteins extracted by enzymatic digestion are capable of preventing the precipitation up to the addition of 125 g/hl.

The other mannoproteins extracted by enzymatic digestion also produce very good results, since any wine which does not have a precipitation at a dose of 75 g/hl is considered to be stable.

The mannoproteins extracted with heat have no effect, even at a very high dosage.

2.—Determining the behaviour at low temperature

This test for the behaviour at low temperature involves keeping the samples at low temperature, at −4° C. for 6 days, once they have been filtered across a membrane with pores of 1 μm.

The absence of any crystallization under these conditions permits the wines tested to be considered as being stable.

The results given in the Table below show the results obtained in respect of different white, rose and red wines.

\*\*\*: crystallization
ND: not determined
O: no crystallization

| Wines | Reference | Meso. acid 10 g/hl | MEC 25 g/hl | MEE1 25 g/hl |
|---|---|---|---|---|
| White 1 | \*\*\* | O | \*\*\* | O |
| White 2 | \*\*\* | O | \*\*\* | O |
| White 3 | \*\*\* | ND | \*\*\* | O |
| White 4 | \*\*\* | ND | \*\*\* | O |
| White 5 | \*\*\* | ND | \*\*\* | O |
| White 6 | \*\*\* | ND | \*\*\* | O |
| Rosé 1 | \*\*\* | ND | \*\*\* | O |
| Rosé 2 | \*\*\* | O | \*\*\* | O |
| Red 1 | \*\*\* | \*\*\* | \*\*\* | O |
| Red 2 | \*\*\* | \*\*\* | \*\*\* | O |
| Red 3 | \*\*\* | \*\*\* | \*\*\* | O |

It will be noted that the mannoproteins extracted by enzymatic digestion of the yeast cell walls prevents the formation of crystals at a dose of 25 g/hl.

The visual result may also be confirmed by determining the difference in concentration of the potassium of the wines in mg/l before and after the cooling down, as shown in the following Tables.

Results obtained with white wine No. 3

| Mannoproteins | 0 g/hl | 15 g/hl | 25 g/hl |
|---|---|---|---|
| MEC | 400 | 350 | 150 |
| MEE1 | 400 | 250 | 0 |
| MEE2 | 400 | 200 | 0 |
| MEE3 | 400 | 300 | 0 |

Results obtained with rose wine No. 1

| Different modalities | Potassium mg/l | Tartaric acid mg/l |
|---|---|---|
| Reference | 80 | 150 |
| MEC 25 g/hl | 30 | 50 |
| MEE1 25 g/hl | 0 | 0 |

The results obtained with the red wines Nos. 1, 2 and 3 correspond to a non-fined red wine, a red wine fined with gelatine at 10 g/hl, and to a red wine fined with egg white at 10 g/hl.

|  | Difference in concentration of potassium mg/l | | |
|---|---|---|---|
| Different modalities | Non-fined wine | Wine fined with gelatine | Wine fined with egg white |
| Reference | 90 | 110 | 180 |
| Meso. acid 15 g/hl | 70 | 70 | 90 |
| Meso. acid 25 g/hl | 0 | 0 | 0 |
| MEC 15 g/hl | 90 | 110 | 130 |
| MEC 25 g/hl | 50 | 50 | 70 |
| MEE1 15 g/hl | 30 | 70 | 70 |
| MEE1 25 g/hl | 0 | 0 | 0 |
| Gum 15 g/hl | 90 | 70 | 140 |
| Gum 25 g/hl | 30 | 50 | 50 |

It will be noted that the mesotartaric acid produces good results starting from 25 g/hl.

The mannoproteins extracted by enzymatic digestion also have an excellent effectiveness at a rate of 25 g/hl, which, again, is the concentration which permits a complete stabilization of the three white, rose and red wines.

The mannoproteins extracted by heat and the gum acacia, in acceptable amounts, do not fully inhibit the tartaric precipitation.

3.—Duration of the effectiveness

Tests have made it possible to compare the effectiveness of the mesotartaric acid and the mannoproteins obtained by enzymatic digestion.

The test involves keeping a treated sample at 30° C. for 10 weeks, and then to expose it to low temperature. The amount of potassium before and after subjecting to low temperature makes it possible to ascertain the tartaric stability of the wine treated with the extract (MEE1) and the instability of the reference wine or the wine treated with mesotartaric acid. Indeed, during its storage at 30° C., the mesotartaric acid hydrolizes and loses its protective power: in addition, it frees the tartaric acid which increases the state of supersaturation of the wine and even promotes the crystallization of the cream of tartar.

| | Difference in concentration of potassium (mg/l) after 6 days at −4° C. |
|---|---|
| Reference | 200 |
| Meso. acid 10 g/hl | 260 |
| MEE1 25 g/hl | 0 |

II/ Proteinic Stabilization

The proteinic stability of wines is determined by a so-called "under heat" test, which involves subjecting the wine to a temperature of 80° C. for 30 minutes. The turbidity is measured by nephelometric analysis, expressed in NTU. The amount of bentonite required is correlated such that the degree of turbidity remains less than 2 NTU.

The following Table shows the results obtained in respect of three white wines treated by different mannoproteins.

| Different modalities | Turbidity NTU | Quantity of bentonite g/hl |
|---|---|---|
| Reference wine 1 | 12 | 80 |
| Wine 1 + MEC 25 g/hl | 12 | 80 |
| Wine 1 + MEE1 25 g/hl | 4.4 | 30 |
| Wine 1 + MEE2 25 g/hl | 4.2 | 30 |
| Wine 1 + MEE3 25 g/hl | 4.3 | 30 |
| Reference wine 2 | 23.1 | 120 |
| Wine 2 + MEC 25 g/hl | 23.4 | 120 |
| Wine 2 + MEE1 25 g/hl | 10.5 | 60 |
| Wine 2 + MEE2 25 g/hl | 10 | 60 |
| Reference wine 3 | 13.8 | 90 |
| Wine 3 + MEC 25 g/hl | 14 | 90 |
| Wine 3 + MEE1 25 g/hl | 6.2 | 50 |
| Wine 3 + MEE3 25 g/hl | 5.8 | 50 |

In respect of the mannoproteins extracted by enzymatic digestion, the results clearly show the reduction in the quantity of bentonite required to obtain stability in the wines. The reduction in the quantity of bentonite is 50%.

Thus, the organoleptic qualities are affected to a relatively minor degree and the wines are especially stabilized in a long-term manner, without altering the taste, since the mannoproteins extracted by enzymatic digestion are neutral in taste.

The tests carried out all show the advantage provided by the mannoproteins extracted by enzymatic digestion, both with regard to inhibiting the tartaric salts, and with regard to the proteinic stabilization of white wines, and this using small quantities.

It is now appropriate to give further attention to the mannoproteins extracted by enzymatic digestion, in order to show the fraction which is likely to be the most effective both with respect to the tartaric salts and with regard to the proteinic stability.

At the outset, the composition of the preparations of mannoproteins extracted with heat and via the enzymatic route may be compared directly. It will be seen in the Table below that the mannoproteins obtained by enzymatic digestion have a distinctly higher protein content.

| Mannoproteins | % of proteins | % of polysaccharides | % of mannose | % of glucose |
|---|---|---|---|---|
| extracted with heat | 4.2 | 93.8 | 92 | 8 |
| extracted enzymatically | 15 | 83.2 | 100 | 0 |

The protein contents are determined by the BRADFORD method (1976) and the polysaccharide contents by the sulphuric phenol method (MONTREUIL and SPIK, 1963).

The hydrolyzable glucide composition of the polysaccharide portion is determined by gas-phase chromatography of the monosaccharides released by hydrolysis with trifluoroacetic acid and derivatives by silylation (LLAUBERES, 1988).

The preparations of mannoproteins extracted with heat (MEC) and of mannoproteins extracted by the enzymatic route (MEE) are analyzed in detail by polyacrylamide gel electrophoresis under denatured conditions (SDS PAGE) permitting a molecular separation, the result of which is shown in the following Table.

| Molecular weight in kda (kilo dalton) | |
|---|---|
| MEC | MEE |
| 77.8 | 77.8 |
| 70 | |
| 44.1 | 44.1 |
| | 41.6 |
| 35.2 | 35.2 |
| 31.8 | 31.8 |
| | 30.3 |
| 27.5 | 27.5 |
| 25.2 | 25.2 |
| 23.2 | 23.2 |
| 21.3 | 21.3 |
| 19.8 | 19.8 |
| 18.4 | 18.4 |
| 17.2 | 17.2 |
| 16 | 16 |
| 15.2 | 15.2 |

The absence of the protein of 70 kda in the MEE and the absence of the proteins of 30.3 kda and 41.6 kda in the MEC will be noted.

The specific proteins in the MEE are then isolated by fractional distillation.

First Test: DEAE sepharose chromatography

The crude MEE extract (100 mg) is solubilized in 1 ml of a pH 8.0 phosphate buffer.

Figure 4:
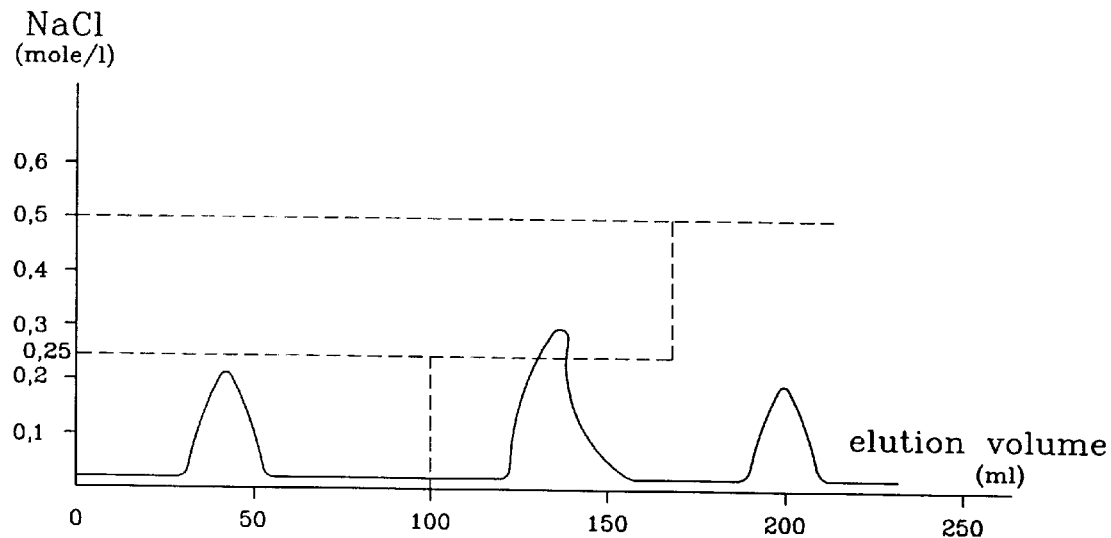
FIG. 4 shows the fractions of proteins obtained by sodium chloride elution.

The DEAE column is washed and then eluted in stages with NaCl 0.25 mole/l, then 0.5 mole/l. 3 ml fractions are collected, and the proteins are determined by measuring the absorption at 280 nm. The fractions which correspond to each of the three peaks are collected, dialyzed against water and are lyophilized (see FIG. 4).

Figure 5:
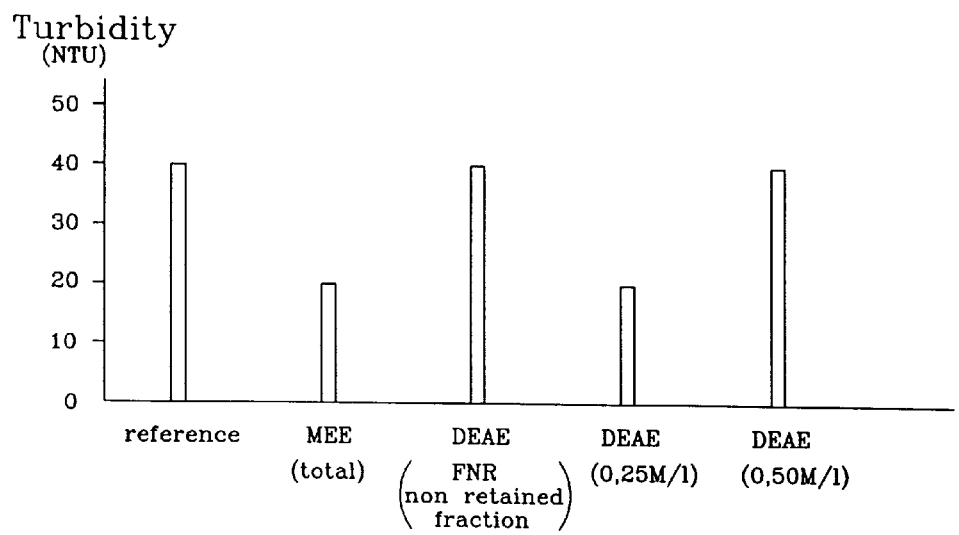
FIG. 5 shows the turbidity index (NTU) in terms of reference wines and wines treated with the different fractions.

25 g/hl are added to a wine which is then subjected to a heat test to determine the proteinic stabilization capacity. The turbidity is measured in NTU. The result is shown in FIG. 5.

The proteinic stabilization capacity of the fraction eluted with 0.25 mole/l of NaCl and the weak effect of the non-retained fraction (FNR) and of the 0.50 mole/l fraction will be noted.

It was possible to determine the protein content and the polysaccharide content of the MEE and of each of the eluted fractions.

As will be seen in the following Table, the fraction which is active at 0.25 mole/l contains 16% protein, 78% polysaccharide, and its extraction yield is 60%.

|  | Yield % | % of proteins | % of polysaccharides |
| --- | --- | --- | --- |
| FNR | 25 | 12 | 86 |
| 0.25 mole/l | 60 | 16 | 78 |
| 0.5 mole/l | 15 | 16 | 81 |

It is thus necessary to purify the 0.25 mole/l NaCl fraction by affinity chromatography with the aid of concanavalin A (Con A), a lectin which binds, in a reversible manner, with the molecules comprising α-D mannopyranosyl and α-D-glucopyranosyl residues.

It is thus possible to separate the proteins and the mannoproteins from this specific 0.25 mole/l NaCl fraction.

The 0.25 mole/l NaCl extract (60 mg) is solubilized in 1 ml of a pH 5 citrate buffer solution and deposited over the Con A sepharose column.

After washing with the buffer solution to elute the proteins, the batch is subjected to an 0.5 mole/l α D-mannoside solution.

Figure 6:
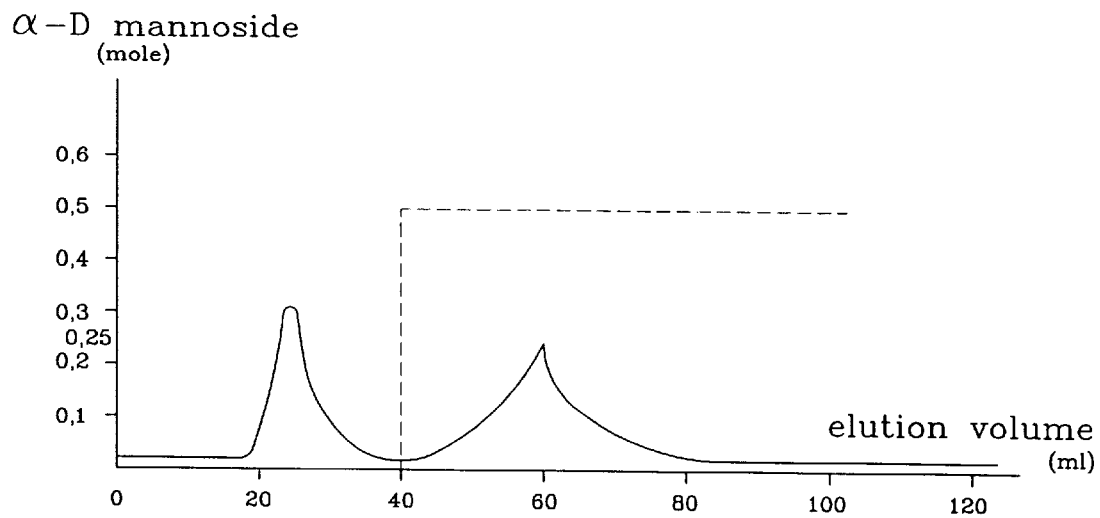
FIG. 6 shows the fractions of proteins obtained by elution with α-D-mannoside.

The mannoproteins are eluted from the gel. 3 ml fractions are collected and the analysis by absorption at 280 nm produces the results shown in the curve of FIG. 6.

The fractions which correspond to each peak are collected, dialyzed against water and lyophilized.

Figure 7:
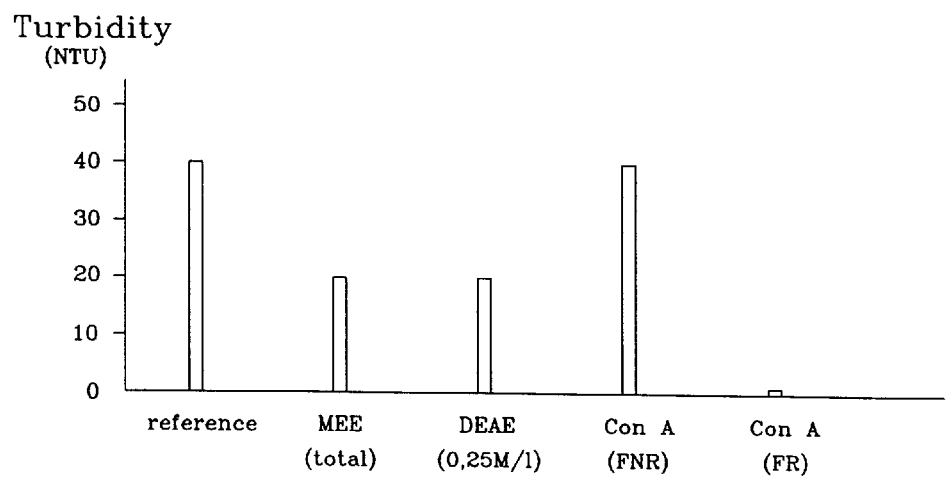
FIG. 7 shows the turbidity index (NTU) in terms of reference wines and wines treated with the different fractions.
Figure 8:
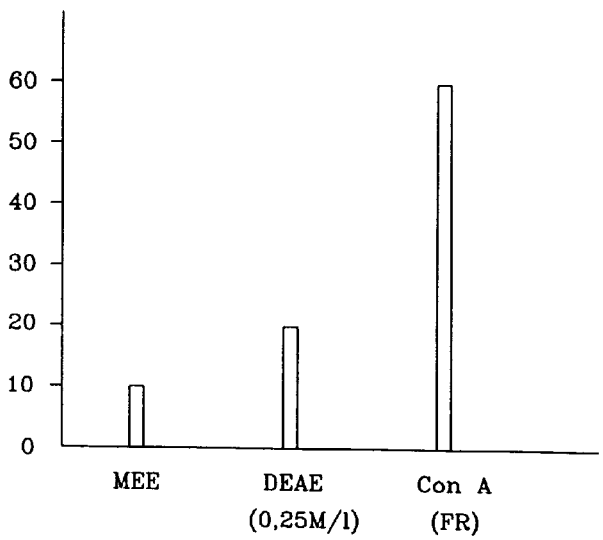
FIG. 8 is a comparison of the concentration of MP 32 in the different fractions.

Each fraction is increased to produce a quantity of 25 g/hl. The heat test gives the results of FIG. 7.

The fraction retained is eluted with 0.5 mole/l α-D-mannoside.

This fraction, and the others, are measured with respect to proteins and polysaccharides.

|  | Yield % | % of proteins | % of polysaccharides |
| --- | --- | --- | --- |
| DEAE (0.25 mole/l) | 60 | 16 | 78 |
| Con A (FNR) | 45 | 20 | 21 |
| Con A (FR) | 15 | 8 | 90 |

The active fraction represents 15% of the MEE.

This fraction comprises 8% of proteins and 90% of mannose.

It is possible, as previously, to carry out a gel electrophoresis (SDS PAGE) which shows that the mannoprotein responsible for the proteinic stability of white wines has a molecular weight of 31.8 kda or MP 32. This is the only protein, the concentration of which increases during purification.

| Molecular weight kda | | |
| --- | --- | --- |
| MEE | DEAE (0.25 mole/l) | Con A (FR) |
| 77.8 | 77.8 | |
|  | 53 | |
| 44.1 | 44.1 | |
| 41.6 | | |
| 35.2 | 35.2 | |
| 31.8 | 31.8 | 31.8 |
| 30.3 | | |
| 27.5 | | |
| 25.2 | | |
| 23.2 | | |
| 21.3 | | |
| 19.8 | 19.8 | 19.8 |
| 18.4 | 18.4 | |
| 17.2 | 17.2 | 17.2 |
| 16 | 16 | 16 |
| 15.2 | 15.2 | 15.2 |

Figure 9:
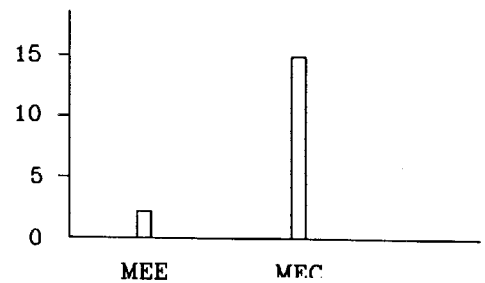
FIG. 9 shows the percentage of MP 32 in the MEC and MEE.

Capillary electrophoresis confirms that the MP 32 is present at 2% in the MEC and at 14% in the MEE; see FIG. 9.

As far as the tartaric stabilization is concerned, the mannoproteins are separated by high-pressure liquid chromatography for molecular separation, according to their dimensions, into two fractions which are dialyzed against water and lyophilized.

The fractions obtained, P1 and P2, are added to a white wine in different quantities. The wines treated are subjected to a cold test and the potassium concentration makes it possible to assess the tartaric crystallization.

After the analysis, it will be noted that the MEE inhibit the crystallization of the potassium tartrate from 15 g/hl. The first fraction P1 does not succeed in inhibiting this crystallization, but by contrast, the fraction P2 permits a tartaric stabilization at a quantity of 5 g/hl.

The analysis of the proteins and polysaccharides contained in the different fractions produces the following results:

|  | % of proteins | % of polysaccharides |
| --- | --- | --- |
| MEE | 15 | 83 |
| P1 | 5.3 | 84.5 |
| P2 | 8.7 | 90.3 |

The fraction P2, which permits a tartaric stabilization, is purified by affinity chromatography by means of the concanavalin (con A) into two fractions, one being a retained fraction (FR) and the other a non-retained fraction (FNR), over lectin, the two fractions being collected, dialyzed and lyophilized.

After addition, in different quantities, to a wine, it is confirmed that the non-retained fraction (FNR) does not contribute to inhibiting the crystallization of the tartaric acid salts.

The retained fraction (FR), itself, makes it possible to prevent the crystallization at an amount of 1.25 g/hl.

The composition of the active fractions may be analyzed afresh.

|        | % of proteins | % of polysaccharides |
|--------|---------------|----------------------|
| P2     | 8.7           | 90.3                 |
| FR con A | 2.5         | 97.5                 |
| FNR con A | 12         | 34                   |

Accordingly, the active fraction comprises 2.5% of proteins and 97.5% of polysaccharides.

It is then necessary to determine, by gel electrophoresis, the molecular substances of the purified fractions.

| Molecular weight in kda (kilo dalton) | | | |
|---|---|---|---|
| MEE | P1 | P2 | FR con A |
| 77.8 | 77.8 | | |
| | | 53.3 | |
| 44.1 | 44.1 | | |
| 41.6 | | 41.6 | 41.6 |
| 35.2 | | 35.2 | |
| 31.8 | 31.8 | 31.8 | 31.8 |
| 30.3 | 30.3 | 30.3 | |
| 27.5 | 27.5 | 27.5 | |
| 25.2 | 25.2 | 25.2 | |
| 23.2 | | 23.2 | |
| 21.3 | | 21.3 | |
| 19.8 | | 19.8 | |
| 18.4 | | 18.4 | |
| 17.2 | 17.2 | 17.2 | 17.2 |
| 16 | 16 | 16 | |
| 15.2 | 15.2 | 15.2 | 15.2 |

The active fraction thus contains only four mannoproteins, the molecular weights of which are 41.6; 31.8; 17.2; 15.2 kda.

The only protein which increases in concentration is the 41.6 kda. Accordingly, this is the mannoprotein responsible for the tartaric stabilization.

This molecule can, however, be extracted solely and exclusively from the cell walls of yeasts by a $\beta$-1-3 and $\beta$-1-6 glucanase compound.

This makes it possible to explain why the mannoproteins extracted by enzymatic digestion have this double stabilization capability with respect to wines, and why they are of such great interest, bearing in mind that the substances used in this process have already been approved by the authorities dealing with this foodstuffs sector.

What is claimed is:

1. Method of treating wine in order to stabilize the wine with respect to tartaric acid and proteinic salts, which comprises:

adding an effective amount of mannoproteins to stabilize the wine, said mannoproteins being extracted from cell walls of yeasts by enzymatic digestion using a mixture of $\beta$-1-3 and $\beta$-1-6 glucanases, said effective amount of mannoproteins being less than 30 g/hl.

2. The method of treating wine according to claim 1, wherein the yeast belongs to a species *Saccharomyces cerevisiae*.

3. The method of treating wine according to claim 1, wherein the effective amount of mannoproteins used in the wine is 25 g/hl.

4. Process for extracting mannoproteins by enzymatic digestion of yeasts for use in the method of treating wine according to claim 1, the process comprising:

incubating the yeast cell walls in an aqueous medium in the presence of $\beta$-1-3 and $\beta$-1-6 glucanases;

separating solid matter; and concentrating a liquid phase by ultrafiltration so as to obtain a product.

5. The process according to claim 4, further comprising: drying the product obtained by lyophilization or atomization to obtain easy manipulation.

* * * * *